US009594042B2

(12) United States Patent
Doerge et al.

(10) Patent No.: US 9,594,042 B2
(45) Date of Patent: *Mar. 14, 2017

(54) ELECTROCHEMICAL DETERMINATION OF FACTOR XA INHIBITORS

(71) Applicant: Roche Diagnostics Operations Inc., Indianapolis, IN (US)

(72) Inventors: Liesel Doerge, Schoenau (DE); Margarete Galm, Penzberg (DE); Carina Horn, Biblis (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 531 days.

This patent is subject to a terminal disclaimer.

(21) Appl. No.: 14/136,769

(22) Filed: Dec. 20, 2013

(65) Prior Publication Data

US 2014/0106383 A1  Apr. 17, 2014

Related U.S. Application Data

(63) Continuation of application No. 12/432,490, filed on Apr. 29, 2009, now Pat. No. 8,636,894, which is a
(Continued)

(30) Foreign Application Priority Data

Oct. 31, 2006  (EP) .................................... 06123234

(51) Int. Cl.
*G01N 27/26* (2006.01)
*C12Q 1/00* (2006.01)
(Continued)

(52) U.S. Cl.
CPC ............. *G01N 27/26* (2013.01); *C12Q 1/005* (2013.01); *C12Q 1/56* (2013.01); *G01N 33/86* (2013.01)

(58) Field of Classification Search
None
See application file for complete search history.

(56) References Cited

U.S. PATENT DOCUMENTS 5,601,995 A  2/1997 Exner
5,677,133 A  10/1997 Oberhardt
(Continued)

FOREIGN PATENT DOCUMENTS

EP  0 360 871  4/1990
WO  WO 9207954  5/1992
(Continued)

OTHER PUBLICATIONS

Bates et al. (Circulation, 2005;112:e53-e60).*
(Continued)

*Primary Examiner* — Matthew Martin
*Assistant Examiner* — Steven E Rosenwald
(74) *Attorney, Agent, or Firm* — McDonnell Boehnen Hulbert & Berghoff LLP (57) ABSTRACT

Methods and devices for determining factor Xa inhibitors, in particular heparins and fractionated or low-molecular-weight heparins, as well as direct factor Xa inhibitors in blood samples. The methods include contacting a blood sample with a detection reagent that contains at least one thrombin substrate having a peptide residue that can be cleaved by thrombin and is amidically bound via the carboxyl end to an electrogenic substance, and with a known amount of factor X reagent and an activator reagent which induces the conversion of factor X into factor Xa. Subsequently, in a second step, the amount or activity of the electrogenic substance that is cleaved from the thrombin substrate by the factor Xa-mediated thrombin activation and/or the time course thereof is determined as the measurement signal using electrochemical methods. In a third
(Continued)

step, the amount of the factor Xa inhibitor in the sample of the blood to be analyzed or a measured quantity that correlates therewith, in particular a clotting time that correlates therewith, is determined on the basis of this measurement signal.

16 Claims, 1 Drawing Sheet

Related U.S. Application Data continuation of application No. PCT/EP2007/009347, filed on Oct. 7, 2007.

(51) Int. Cl.
 *C12Q 1/56* (2006.01)
 *G01N 33/86* (2006.01)

(56) References Cited

U.S. PATENT DOCUMENTS

| | | |
|---|---|---|
| 5,702,912 A | 12/1997 | Hemker et al. |
| 5,762,770 A | 6/1998 | Pritchard et al. |
| 6,270,637 B1 | 8/2001 | Crismore et al. |
| 6,994,984 B2 | 2/2006 | Gempeler et al. |
| 2003/0146113 A1* | 8/2003 | Unkrig .......... C12Q 1/005 205/792 |
| 2005/0196820 A1 | 9/2005 | Zweig |
| 2006/0166284 A1 | 7/2006 | Light et al. |

FOREIGN PATENT DOCUMENTS

| | | |
|---|---|---|
| WO | WO 9310262 | 5/1993 |
| WO | WO 9900515 | 1/1999 |
| WO | WO 0077246 | 12/2000 |
| WO | WO 0144493 | 6/2001 |
| WO | WO 03050298 | 6/2003 |
| WO | WO 2005031303 | 4/2005 |

OTHER PUBLICATIONS

Hirsh, et al., "Heparin and Low-Molecular-Weigh Heparin (Mechanisms of Action, Pharmakokinetics, Dosing, Monitoring, Efficacy and Safety)", Chest, 119:64-94 (2001).

* cited by examiner

ELECTROCHEMICAL DETERMINATION OF FACTOR XA INHIBITORS

CROSS REFERENCE TO RELATED APPLICATION

This is a continuation of U.S. patent application Ser. No. 12/432,490, filed Apr. 29, 2009, now U.S. Pat. No. 8,636,894 B2, which is a continuation of International Application PCT/EP2007/009347, which has an international filing date of Oct. 7, 2007. PCT/EP2007/009347 claims the benefit of European Patent Application No. EP06123234.4, filed Oct. 31, 2006. PCT/EP2007/009347 is incorporated by reference herein.

BACKGROUND OF THE INVENTION

Field of the Invention

The invention concerns methods for the electrochemical determination of factor Xa inhibitors, especially of heparins and heparin derivatives as well as direct factor Xa inhibitors in blood samples.

In addition the invention concerns test elements based on dry chemistry and test element analytical systems for the electrochemical determination of factor Xa inhibitors, especially of heparins and heparin derivatives as well as direct factor Xa inhibitors in blood samples.

Description of Related Art

Anticoagulants which in particular also include heparins are often used in clinical practice for the prophylaxis and therapy of haemostatic disorders (disorders of the coagulation system). Heparins and heparin derivatives are used especially for the therapy and prophylaxis of thromboembolic diseases. They are very effective in the prophylaxis and treatment of leg vein thromboses, pulmonary embolisms and for treating unstable angina pectoris and acute myocardial infarction. They are also often used during operations and in particular for cardiological procedures (bypass) and for blood transfusions.

The action of heparins is mainly based on their interaction with antithrombin III (ATIII) as a result of which they change the conformation of ATIII. This accelerates the inactivation of certain coagulation enzymes (thrombin (FIIa), factor Xa (FXa) and factor IXa) and thus coagulation is prolongated. Heparins can thus be classed as factor Xa inhibitors. Other factor Xa inhibitors are for example certain oligo-saccharides such as the pentasaccharide Fondaparinux or low-molecular-weight direct factor Xa inhibitors which are still in clinical development and can be assigned to different classes of substance. In addition to unfractionated heparins (UFH) which have been used for a long time, various fractionated heparins or low-molecular-weight heparins (LMWH) have been used since the end of the 1980s. Fractionated heparins have now replaced the UFHs for many indications and are prepared from unfractionated heparins by chemical or enzymatic depolymerization to form fragments which have only about ⅓ of the size of the standard heparin. This weakens among others the effect of these LMWHs on thrombin whereas factor Xa is preferentially inactivated. Fractionated heparins have other advantages over conventional unfractionated heparins as a result of their more advantageous pharmacokinetics. A review of these classes of substance with regard to their clinical action and significance may be found in "Heparin and Low-Molecular-Weight Heparin" (Mechanisms of Action, Pharmakokinetics, Dosing, Monitoring, Efficacy and Safety), Hirsh et al.; Chest 2001; 119:64 p-94 p.

Patients which have been administered unfractionated heparin are required to be monitored due to the individual variability of the bioavailability, the protein binding and short half-life of 30-150 minutes in order to avoid a possible overdose with an increased bleeding tendency or an underdose with an increased risk of thrombosis. In the clinical routine treatment with UFH this is most frequently monitored using the activated partial thromboplastin time (aPTT) and also by the thrombin clotting time (TCT) or activated clotting time (ACT). These assays are so-called global assays because they unspecifically reflect the thrombin-induced formation of a fibrin clot. The aPTT test which primarily determines the activity of the factors of the intrinsic system, is mainly sensitive to the inhibitory effects of heparin on thrombin. The aPTT test is sensitive for the heparin range of 0.1-0.7 U/ml but the normal range of aPTT as well as its therapeutic range depend very strongly on the reagent and the analyzer that is used. Another limiting factor is sample stability which often results in falsified results particularly after the blood sample has stood for too long. Further disadvantages of such global coagulation assays are among others the often complex experimental procedure which requires specially trained personnel to achieve reproducible results and the relatively high reagent consumption of these tests.

Monitoring is not absolutely necessary for normal patients when administering low-molecular-weight heparins due to their improved pharmacokinetics. However, it is recommended that the therapy is checked at the start of treatment and it is necessary especially in the case of patients with renal insufficiency due to their changed renal excretion and is recommended for patients with an extreme body weight, newborns, children and pregnant women or when they are used for several weeks or after fresh traumas or operations.

In clinical routine aPTT is used above all to monitor LMWH although this test has an only inadequate sensitivity for this anticoagulant and is moreover dependent to a very strong degree on the detection reagent that is used.

An FXa test is a suitable detection test for monitoring the effect of low-molecular-weight heparins.

Previous FXa tests are usually carried out as chromogenic tests or as clotting tests where the chromogenic tests measure factor Xa activity and the clotting test measures coagulation. Both test principles follow the same test procedure:

1. FXa+[heparin/antithrombin III]→[FXa/heparin/ATIII] complex+remaining FXa
2. a) remaining FXa cleaves a chromogenic residue from a FXa-specific substrate (chromogenic test)
   b) remaining FXa cleaves prothrombin to form thrombin (coagulation test via thrombin-induced fibrin cross-linking)

When the sample is added, factor Xa which is present in a defined amount in the test reagent binds with the heparin and antithrombin III contained in the sample and forms an inactivated complex with them. The remaining factor Xa cleaves either the chromogenic substrate or forms thrombin with the other coagulation factors contained in the sample and the thrombin cleaves fibrinogen to form fibrin (clot formation). More or less substrate is cleaved depending on the activity of factor Xa. The activity of factor Xa in turn depends on the amount of heparin contained in the sample. Whereas the chromogenic tests are specific for the FXa activity in the sample, coagulation tests do not exclusively measure the FXa activity but are nevertheless often more sensitive for LMWH than aPTT.

Several chromogenic tests but only a few coagulation tests (Heptest from the Sigma Company, ENOX test from the Pharmanetics Company) are commercially available. The various tests correlate only moderately with one another and with aPTT because they have different end points. The chromogenic tests yield activities but not clotting times. However, there is only a moderate correlation between the clotting time and factor Xa activity. Furthermore, these chromogenic tests require a separation of the plasma and they cannot be used directly in whole blood samples. As a result of the complicated sample preparation and process steps and the required devices, these methods of determination are time-consuming, labour intensive and require complicated apparatuses. Although the Heptest yields a clotting time as a result, it can, however, be very different depending on the different heparin sensitivity of the patient at the same heparin concentration. Furthermore, it is necessary to establish a heparin calibration curve from which the test result can then be read. Up to now only a single factor Xa test has been available as a dry chemistry test and thus also suitable for point-of-care instruments (ENOX test from the Pharmanetics Co.) which is carried out using a test card on the Rapid Point analyzer from Bayer AG. This test was specially developed for the use of Enoxaparin for percutaneous transluminal angioplasty and only distinguishes between Enoxaparin concentrations of >1 U/ml and <1 U/ml and is thus unsuitable for the routine monitoring of low-molecular-weight heparins especially because other fractionated heparins and unfractionated heparin interfere with the test.

WO 03/050298 describes the principle of this dry chemistry FXa test as follows: The sample to be examined which is preferably citrated whole blood, is admixed with a dry chemistry reagent which contains at least a factor Xa activator, preferably Russels viper venom and homogeneously dispersed magnetic particles. Factor X contained in the sample is converted into factor Xa by the factor Xa activator contained in the reagent and the factor Xa in turn results in the conversion of fibrinogen into fibrin via the prothrombin-thrombin conversion and thus the formation of the coagulation clot. This clot is detected by means of optical methods by observing the mobility of the magnetic particles in the reaction mixture which is caused by an external oscillating magnetic field. Hence this test principle is based on the formation of a fibrin clot which is only formed during the course of the detection reaction in a multistage reaction cascade triggered by factor Xa which involves further enzymes and cofactors in addition to factor Xa. Thus, for example the polymerization and cross-linking of fibrin requires the presence of calcium ions and activated factor XIIIa which is in turn formed from inactive factor XIII by a thrombin-dependent activation. Hence, the determination of factor Xa by means of the determination of a fibrin clot is also dependent on other essential factors and possible interfering effects. In addition to this indirect method of determination, the detection method described in WO 03/050298 requires a complex detection and evaluation system for the factor Xa determination. Thus, on the one hand, the test carrier on which the coagulation reaction takes place must have special devices which ensure a good and homogeneous mixing of the reagents and magnetic particles with the sample and, on the other hand, the evaluation system for determining the factor Xa activity must have devices for generating an oscillating magnetic field for example by means of a movable permanent magnet and optical systems for illuminating and photometrically detecting the movement of the magnetic particles.

WO 01/63271 (US2003/0164113) describes in general electrochemical sensors based on dry chemistry for determining blood coagulation or individual coagulation factors which have at least two electrodes on an inert carrier, as well as a dry reagent which contains a protease substrate which consists of a peptide residue that can be cleaved by a protease of the blood coagulation system and is amidically bound via its carboxyl end to substituted amines and in particular to a phenylenediamine residue. After the protease-induced cleavage, these substituted amines act as electron carriers of the 2nd type and can be used for the electrochemical determination of the protease activity. In addition to the so-called global tests such as aPTT, PT or ACT in which the clotting time is determined via the activity of the protease thrombin, WO 01/63271 (US2003/0164113) also describes tests that can be used to determine individual coagulation factors or their inhibitors. In this case WO 91/63271 teaches the use of substrates especially designed for the coagulation factor to be determined, the peptide part of which is specially adapted to the protease to be determined such that it can be specifically cleaved by this protease and the substituted amine as an electrochemically detectable particle specifically reflects the activity of this protease. When applied to a factor Xa test this would mean using a protease substrate which consists of a peptide residue that can be cleaved by factor Xa whose carboxyl end is amidically bound to substituted amines and especially to a phenylenediamine residue. To this extent the test principle is similar to that of chromogenic factor Xa tests in which an enzymatic cleavage product of a factor Xa-specific substrate is also used to determine factor Xa.

Accordingly, the inventors have identified a need in the art to provide methods for determining factor Xa inhibitors in blood samples which can be carried out simply even by persons that are not specially trained with low requirements with regard to time, apparatus or labor and which lead to reliable results in a short time. In particular, what is needed is a method for determining factor Xa inhibitors in blood samples which can be simply carried out and managed with the smallest possible number of process steps and required reagents and/or apparatuses thus enabling a rapid decentral analysis for example directly in intensive care units or hospital wards. It is desirable that the methods and devices for determining factor Xa inhibitors in blood samples also enable a determination directly in whole blood and thus do not require any complicated sample preparation steps. The methods and devices for determining factor Xa inhibitors in blood samples could satisfy the requirements for shelf-life and stability of reagents and enable a determination which is as accurate and specific as possible. In particular, a need exists for the above methods and devices for determining heparins, in particular fractionated heparins or low-molecular-weight heparins as well as direct factor Xa inhibitors in blood samples.

SUMMARY OF THE INVENTION

In one aspect, the invention is directed to a method for determining a factor Xa inhibitor in a blood sample. The method includes contacting a blood sample with a known amount of factor X reagent, an activator reagent that induces the conversion of factor X into factor Xa, and a detection reagent including a peptidic thrombin substrate that can be cleaved by thrombin and having a carboxyl end that is amidically bound to an electrogenic substance. The method further includes measuring the amount or activity of the electrogenic substance that is cleaved from the thrombin substrate by measuring an electrochemical signal associated with the amount or activity of the electrogenic substance, and determining the amount of the factor Xa inhibitor in the sample by relating the amount or activity of the electrogenic substance to the amount of Xa inhibitor in the sample.

In various aspects of the invention, the factor X reagent is added to the sample spatially separated from or at a separate time from the addition of the activator reagent to the sample. Also, the factor X reagent and activator reagent may be present together in a dry state and factor X is not converted into factor Xa until contact with the sample.

Another aspect of the invention is directed to a test element for determining a factor Xa inhibitor, the element having an inert carrier having at least two electrodes, a detection reagent that contains at least one peptidic thrombin substrate that can be cleaved by thrombin and having a carboxyl end that is amidically bound to an electrogenic substance, a factor X reagent and an activator reagent for converting factor X into factor Xa.

In various aspects of the invention, the activator reagent is present on the test element at least partially spatially separated from the factor X reagent. Also, the activator reagent may be arranged at least partially in front of the factor X reagent in a flow direction of the sample.

In a further aspect, the invention is directed to an electrochemical test element analytical system having at least one device for measuring current or voltage and a test element as summarized above.

DETAILED DESCRIPTION

The present invention provides methods, electrochemical test elements and test element analytical systems for determining factor Xa inhibitors in blood samples. More particularly, the present invention describes methods for determining factor Xa inhibitors in blood samples which are characterized in that in a first step a sample of the blood to be analyzed is brought into contact with a detection reagent which contains at least one thrombin substrate which consists of a peptide residue that can be cleaved by thrombin and which is amidically bound via the carboxyl end to an electrogenic substance, and with a known amount of factor Xa, subsequently in a second step the amount or activity of the electrogenic substance which is cleaved from the thrombin substrate by the factor Xa-mediated thrombin activation and/or its time course is determined as the measurement signal using electrochemical methods, and finally in a third step the amount of the factor Xa inhibitor in the sample of the blood to be analyzed or a measured quantity that correlates therewith, in particular a clotting time that correlates therewith, is determined on the basis of this measurement signal.

According to the invention the known amount of factor Xa is not added directly as a factor Xa reagent in the first step of the method but rather takes place by adding a known amount of factor X reagent and an activator reagent to the sample which results in the conversion of factor X into factor Xa.

The method according to the invention is further elucidated on the basis of an illustrative example:

The test principle is based on the determination of the enzymatic activity of thrombin formed as a result of the factor Xa-induced coagulation reaction by means of an electrochemical measurement in which at least one cleavage product is determined electrochemically on the electrodes. A tripeptide substrate such as for example reduced Chromozym TH (tosyl-glycy-prolyl-arginine-4-nitroanilide acetate) which has amidically bound an electrogenic substance via the carboxyl end of the tripeptide moiety can be used in particular as a thrombin-specific substrate. Such electrogenic substances are described for example in WO 01/63271 (US2003/0164113) and can in particular be substituted anilines, especially nitroaniline derivatives or phenylene-diamines. The detection reaction proceeds as follows:

The enzyme thrombin cleaves an electrogenic substance from the substrate which in the present example is phenylenediamine which is oxidized on the electrodes to phenylenediamine. In a preferred embodiment an auxiliary substance is reduced at the same time as the oxidation of this cleavage product for example of resazurin to resorufin as a result of which a current intensity can be measured which correlates with the amount of cleavage product. Thus, in the present electrochemical reaction, resazurin is reduced as an auxiliary substance on the cathode whereas phenylenediamine is oxidized on the anode. A two-electrode system is preferably used for the electrochemical measurement of thrombin activity in which the potential on the working electrode is, on the one hand, selected to be high enough that the phenylenediamine released from thrombin is oxidized and, on the other hand, low enough that no residual group of the tripeptide is reduced. The potential difference between the cathode (working electrode) and the anode (counter electrode) is controlled by a potentiostat. In the present example a potential difference of about 550 mV can be selected as a suitable potential difference in order to enable only the desired reactions to occur at the electrodes.

With regard to the method according to the invention this electrochemical test principle is used in a factor Xa inhibitor test as follows:

In the reaction mixture there is, in addition to the detection reagent, a known amount of factor Xa which is formed by adding a known amount of factor X reagent and an activator reagent which converts factor X into factor Xa. The blood sample to be analyzed contains the factor Xa inhibitor to be determined which is preferably a heparin. This inhibitor forms a stoichiometric complex with the factor Xa which is present in the reaction mixture in a known amount and in excess and antithrombin III which is present in the blood sample. In this process a residual amount of factor Xa remains, the concentration of which depends on the concentration of the factor Xa inhibitor in the sample. This can now react with the prothrombin present in the blood sample (and with the factor Va which is also present there) to form a prothrombin complex and subsequently thrombin which, as described above, can be determined by a thrombin-dependent enzymatic cleavage of an electrogenic substance and the electrochemical detection of the substance.

The more factor Xa inhibitor is present in the sample, the less residual factor Xa remains after the complex formation with ATIII and the less thrombin is formed. The present measuring principle does not detect a clotting time in the strict sense i.e. it is not a clotting test with the formation of fibrin but rather a determination of the time course of thrombin formation by electrochemical methods.

Figure 1:
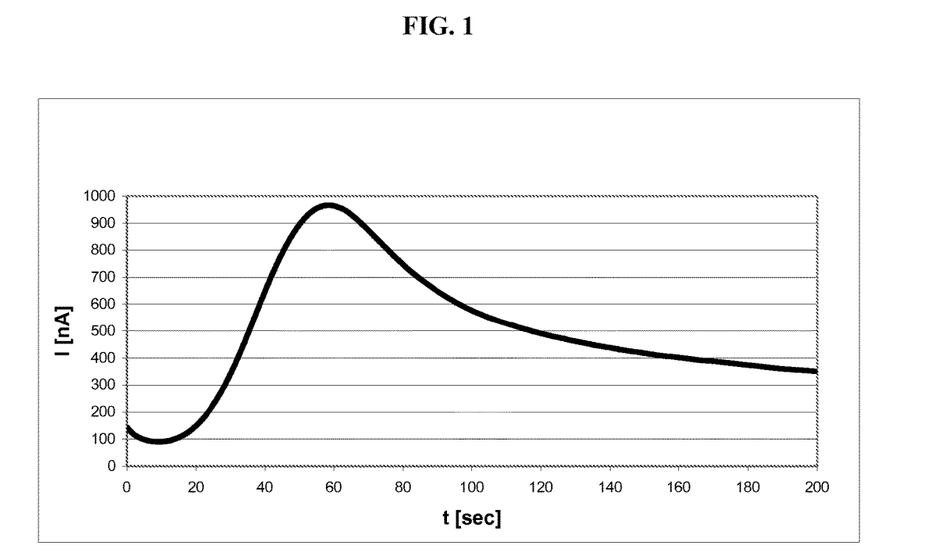
FIG. 1 shows an example of the primary measured result of an electrochemical factor Xa inhibitor determination corresponding to the methods according to the invention.

Example 2 and FIG. 1 show the result of such an electrochemical thrombin determination according to the inventive methods as an example.

The use according to the invention of activated factor Xa with a thrombin detection reagent gives more information about the physiological state of the coagulation system compared to chromogenic factor Xa tests and the methods described in WO 01/63271 (US2003/0164113) because in this case it is not an artificial factor Xa-specific substrate which is cleaved and used to measure the factor Xa activity but rather firstly thrombin is formed as in the physiological coagulation. This formation of thrombin can according to the invention be determined electrochemically using a thrombin-specific substrate and converted for example into clotting times using a suitable algorithm. Compared to factor Xa inhibitor tests such as the Heptest or the ENOX test which are based on the determination of the factor Xa-induced formation of a fibrin clot, the invention has the advantage that the determination by means of electrochemical methods is much more simple and can be carried out less labour-intensively and with simpler equipment. Since the factor Xa activity is determined with the method according to the invention by the activity of the first naturally occurring coagulation factor (thrombin) which is downstream thereof in the physiological coagulation cascade, the physiological activity of the factor Xa inhibitor is determined, on the one hand, in a manner that is closer to the natural system than with chromogenic tests and the methods described in WO 01/63271 (US2003/0164113) which use unphysiological factor Xa substrates and, on the other hand, the detection of the factor Xa activity is carried out at an earlier point in the coagulation cascade than is the case with tests that are based on the determination of the factor Xa-induced formation of a fibrin clot so that the downstream coagulation factors between thrombin formation and fibrin clot formation have no effect on the determination of factor Xa activity. This allows more accurate and more specific information to be obtained about factor Xa activities in the physiological system than with the previously known tests.

The inventive solution allows a factor Xa inhibitor determination especially also in whole blood because, in contrast to chromogenic measuring methods, it is not necessary to separate interfering and in particular coloured blood components in the electrochemical methods that are used. By matching the control of the electrodes to the electrogenic substances used for the detection for example by adapting the selected electrode potential, it is possible to detect the electrogenic substances used for the detection substantially uninfluenced by other potentially interfering substances occurring in the sample or the reagents.

In order to determine a factor Xa inhibitor it is necessary according to the invention to add at least the following substances to the sample to be examined or they must be present in the sample: A known amount of factor X, an activator reagent and a peptidic thrombin substrate as the detection reagent from which an electrogenic substance can be enzymatically cleaved off.

Many of the known thrombin substrates used in thrombin tests including the widely used Chromozym TH do not, however, have an absolute and exclusive thrombin specificity but rather can also be cleaved by other enzymes.

The coagulation factor Xa is a serine protease which naturally recognizes the amino sequence -Ile-Glu-Gly-Arg- of prothrombin and by cleaving this sequence, activates the natural substrate prothrombin to form thrombin. In addition to this physiological substrate, factor Xa is also able to enzymatically cleave other peptides having this or other cleavage sequences. Thus, peptidic thrombin substrates and in particular the widely used Chromozym TH can also be cleaved by factor Xa. This low substrate specificity of factor Xa can result in problems in the methods according to the invention especially when such a thrombin substrate which can also be cleaved by factor Xa is used as a detection reagent and already comes into contact with factor Xa before adding the sample and can be converted thereby. As a result a portion of the thrombin substrate can already be converted such that this is no longer available for the thrombin-mediated detection reaction and thus the result of the measurement is affected. Such undesired side reactions can occur especially when factor Xa and the thrombin substrate are in contact over a long period such as would be for example the case if these two substances were to be introduced simultaneously into a liquid detection reagent.

With regard to the previously mentioned exemplary measuring system this would mean that if factor Xa and the reduced Chromozym TH used as a thrombin substrate were already able to react with one another over a long period before the start of the detection reaction, a portion of the thrombin substrate would already be cleaved and thus a largely undefined amount of the cleaved electrogenic substance would already be present in the reagent. Such cases can occur especially when the two substances are present together in a liquid reagent or in the case of dry chemistry tests, came into contact in liquid form during their production. Thus, a common dwelling time of 2 h may already be sufficient to cleave about 25% of the reduced Chromozym TH that is present due alone to the action of factor Xa. The result of such a factor Xa-induced premature substrate degradation would in the case of the electrochemical method according to the invention be in particular that the measurement signal is offset towards higher current strengths and also has high current strengths at the minimum already before the start of the thrombin-induced cleavage of the reduced Chromozym TH because phenylenediamine that has already been released in the sample due to the enzymatic action of factor Xa is present as an electrogenic substance.

According to the invention the problem of premature factor Xa-induced substrate degradation is at least partially solved in that a known amount of factor Xa is obtained in the reaction mixture by adding a known amount of factor X reagent and an activator reagent to the sample which results in the conversion of the proteolytically inactive factor X into the proteolytically active factor Xa.

Surprisingly this method according to the invention has shown that a particularly simple and stable test element assembly can be achieved by this reagent combination. The fact that no activated factor Xa but rather inactive factor X is present in the reagent before adding or activating an activator reagent, enables the detection reagent to be already brought into contact with factor X before the start of the determination reaction without a premature factor Xa-induced substrate degradation and thus interference with the determination occurring.

In particularly preferred embodiments an activator or a complex involved in the extrinsic pathway of plasmatic coagulation is used as an activator reagent. In particular naturally occurring activators or coagulation factors such as tissue factor and/or factor VIIa can be used as activator reagents and it is also possible to use other activators such as synthetically produced activators in addition to the naturally occurring activators or coagulation factors.

In further preferred embodiments an activator or a complex involved in the intrinsic pathway of plasmatic coagulation is used as an activator reagent. In particular naturally occurring activators or coagulation factors such as factor XIIa or substances which result in a conversion of factor X into factor Xa such as Russels Viper Venom (RVV-X) can be used as activator reagents, and other activators such as synthetically prepared activators can also be used in addition to these naturally occurring activators.

In this case the activator reagent can be added as an external reagent to the sample or to the other reagents before or during the course of the measurement or it can already be present in the blood sample. This also applies similarly to further substances that are necessary for the process of factor Xa activation or for the detection reaction. Thus, in particular further required coagulation factors such as factor V or antithrombin can be provided by the blood sample to be analyzed.

In a particularly preferred embodiment of this variant factor X reagent is added to the sample spatially or chronologically separated from the addition of the activator reagent to the sample.

The separation of factor X reagent and activator reagent avoids an undesired premature conversion of factor X into factor Xa. This is the basis for an amount of factor Xa that is known as accurately as possible at the beginning of the measurement which in turn has a decisive influence on the determination of the factor Xa inhibitor. In this case the addition of factor Xa reagent to the sample is spatially and/or chronologically separated from the addition of the activator reagent to the sample.

Dry chemistry reagents are usually applied to test elements by applying them as a solution in a line-shape on the test element and removing the solvent there so that they are present there in a dry chemistry form. This is particularly advantageous since reagents in a dry chemistry form often meet substantially higher requirements with regard to shelflife and stability than wet chemistry reagents. Transfer into the more active but also more unstable dissolved form occurs at a given time by redissolving the dry chemistry reagents by supplying liquid and preferably by directly dissolving them in the blood sample to be analyzed.

The ability to arrange different reagents in different compartments on a test element substantially prevents contact between these reagents until the start of the factor Xa inhibitor determination. This also allows undesired side reactions of these reagents to be largely suppressed. The reagents present in the various compartments are preferably only brought into contact with another by the sample liquid. In wet chemistry methods this can for example be achieved in that the reagent solutions are present in different liquid spaces and only come into contact with the sample at the start of the factor Xa inhibitor determination for example in that they are added from these spaces to the sample by means of a pump or in that sample flows successively through the different liquid spaces.

Preferred methods and devices which result in a spatially or chronologically separated addition of activator reagent and factor Xa reagent to the sample can in particular be configured in the form of separate reagent lines.

In order to determine factor Xa inhibitors according to the invention a detection reagent must also be present in addition to the factor X reagent and the activator reagent. These reagents can be present before the start of the determination in at least partially spatially separated compartments. Since according to the present invention no factor Xa should be present before the start of the detection reaction, it is also possible in preferred embodiments that the factor X reagent or the activator reagent is present together with the detection reagent. This also applies similarly in the case of wet chemistry methods to the bringing together and mixing of reagents. Thus in this case the factor X reagent or the activator reagent can be present together with the detection reagent in a reagent solution. Factor Xa is not formed until the missing reagent component (factor X reagent or activator reagent) has been added to this reagent mixture.

These reagent mixtures make methods of determination and devices possible which require fewer process steps or reagent compartments and are thus easier and more cost-effective to manufacture and easier to handle.

In a particularly preferred embodiment the factor X reagent is a component of the detection reagent and the addition of this detection reagent/factor X reagent combination to the sample is spatially or chronologically separated from the addition of the activator reagent to the sample.

Preferred methods and devices which allow the activator reagent and detection reagent/factor X reagent combination to be added to the sample in a spatially separated manner or at separate times can be designed similarly to the previously described methods and devices which allow activator reagent and factor X reagent to be added to the sample in a spatially separated manner or at different times, in particular in the form of separate reagent lines.

In particular the detection reagent/factor X reagent combination can be added after the addition of the activator reagent. In a preferred embodiment the reagents are spatially separated by arranging reagent lines consecutively in the flow direction of the sample and thus their reagents are successively activated by the sample which corresponds to a staggered addition to the sample. In this case the reagent lines can be present separated from one another or can also be in contact with one another, for example be adjacent to one another or also be entirely applied on top of one another or partially staggered. In a particularly preferred embodiment the reagent line of the activator reagent is at least partially applied in front of the reagent line of the detection reagent/factor X reagent combination in the flow direction of the sample preferably in the form of partially overlapping reagent lines or reagent lines lying above one another where in the latter case the reagent line of the activator reagent is applied over the reagent line of the detection reagent/factor X reagent combination.

Figure 2:
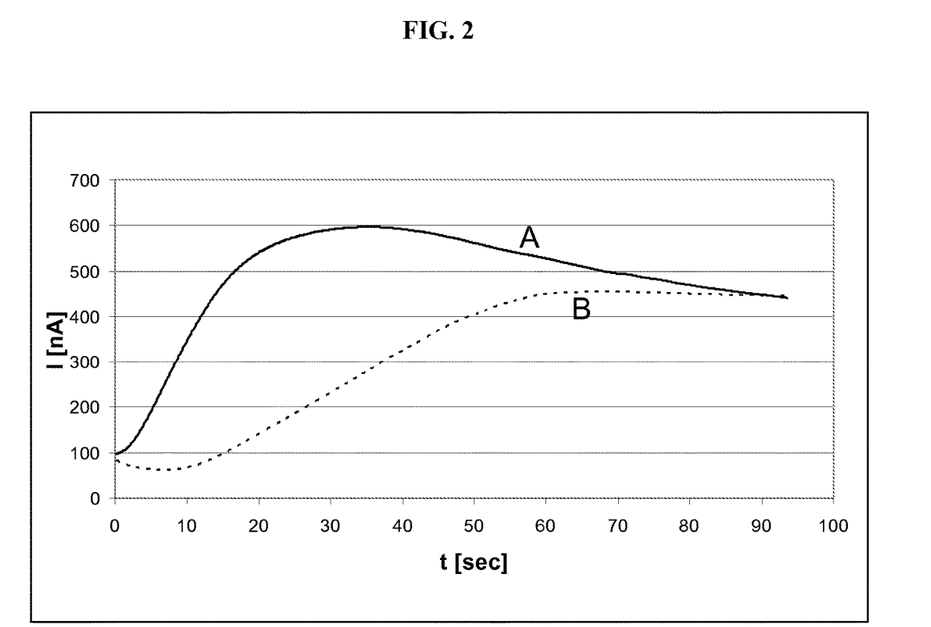
FIG. 2 shows the results of electrochemical thrombin determinations with different arrangements of reagent lines of an activator reagent and a detection reagent/factor X reagent combination on a test element.

Example 3 and FIG. 2 show examples of electrochemical thrombin determinations with different arrangements of reagent lines of the activator reagent and the detection reagent/factor X reagent combination on a test element.

In a further preferred embodiment of this variant the factor X reagent is added to the sample in a common step with the addition of the activator reagent to the sample.

In the case of wet chemistry reactions this can for example be carried out by jointly adding both reagents to the sample from their respective storage compartments (storage containers) for example by means of pumps or pipettes. It is, however, also possible that the factor X reagent and activator reagent are firstly added to one another and this reagent mixture in which factor Xa forms is then added to the sample.

In a particularly preferred embodiment the factor X reagent and activator reagent are both present in a dry state and factor X is only converted into factor Xa by contact with the sample.

The use of dry chemistry reagents enables them to be stored together in an inactivated form without a chemical reaction taking place between the reagents. The reagents are not converted into a state in which they can react with one another until the dry chemistry reagents are wetted. This "activation" of the dry chemistry reagents is affected by the liquid blood sample itself in a preferred embodiment.

In a particularly preferred embodiment factor X reagent, activator reagent and detection reagent are present as dry chemistry reagents and factor X is not converted into factor Xa until contact with the sample.

Since the use of dry chemistry reagents allows them to be stored together in an inactivated form without a chemical reaction occurring between the reagents, these methods and devices according to the invention allow all reagents necessary for determining factor Xa inhibitors to be stored in a common compartment without a premature factor Xa-induced thrombin substrate degradation occurring. Only when the liquid sample is added, is factor X converted into factor Xa with a substantially defined starting point and time course so that finally a known amount of factor Xa is present in the sample which forms the basis for determining factor Xa inhibitors according to the principle of the invention. This basically allows all reagents necessary to determine factor Xa inhibitors to be combined in a single dry chemistry reagent line or spot using methods known to a person skilled in the art which enables a simple and cost-effective production and a simple and less error-prone handling.

The methods and devices according to the invention for determining factor Xa inhibitors can be used especially advantageously to determine heparins and in particular fractionated or low-molecular-weight heparins. Other factor Xa inhibitors that can be advantageously determined using the methods and devices according to the invention can be in particular indirect selective or direct factor Xa inhibitors.

Factor Xa inhibitors in the sense of the invention can be regarded as all substances which directly or indirectly influence the activity of factor Xa and in particular reduce the activity and thus have an influence on and in particular retard the blood coagulation cascade process. Direct factor Xa inhibitors have a direct effect on factor Xa and thus influence its activity whereas indirect factor Xa inhibitors do not directly interact with factor Xa but rather have an effect on its quantity and formation or require a cofactor for their activation. They may for example be anticoagulants which act on coagulation factors which are present in the coagulation cascade before factor Xa and are involved in its formation and/or regulation. Examples of indirect selective factor Xa inhibitors are certain pentasaccharides such as Fondaparinux and Idraparinux which act in cooperation with antithrombin III and, in contrast to the heparins, are selective for factor Xa. Examples of direct Xa inhibitors are Otamixaban or Razaxaban.

Another aspect of the present invention concerns test elements with an electrochemical sensor on a dry chemistry basis for determining factor Xa inhibitors, in particular unfractionated heparins, fractionated or low-molecular-weight heparins, indirect selective factor Xa inhibitors or direct factor Xa inhibitors, which, on an inert carrier, has at least two electrodes and a detection reagent which contains at least one thrombin substrate which consists of a peptide residue that can be cleaved by thrombin and is bound amidically via the carboxyl end to an electrogenic substance, as well as at least a certain amount of factor X reagent and an activator reagent.

Such test elements according to the invention are particularly suitable for carrying out the previously described methods according to the invention for determining factor Xa inhibitors in blood samples.

Test elements according to the invention are in particular electrochemical test elements on a dry chemistry basis. Such test elements contain at least two electrodes of which at least one electrode is a so-called working electrode. They do not necessarily contain a classical reference electrode such as for example an Ag/AgCl reference electrode but rather merely at least one working electrode and one counter electrode. The electrodes can be constructed from all current electrode materials such as metals, noble metals, alloys or graphite and preferably from noble metals such as gold or palladium, or graphite. The different electrodes of the test element can consist of the same or different materials. In a particularly preferred embodiment the test element contains a working electrode and a counter electrode which both consist of gold.

Specific embodiments of such electrochemical test elements especially with regard to the choice of materials, arrangement of electrodes and reagents as well as the manufacture of test elements are described in the prior art for example in U.S. Pat. No. 5,762,770, U.S. Pat. No. 6,270,637 or WO 01/63271 (US2003/0164113) and are known to a person skilled in the art.

In preferred embodiments the reagents are applied to the electrodes in the form of one or more reagent lines. These can be present separate from one another or partially or completely overlap. Furthermore, according to the invention it is possible to apply and dry the reagents not directly on the electrodes but rather in the vicinity of the electrodes for example on a flat substrate next to the electrodes. In this case the reagents are transported with the sample to the electrodes during the measurement. Alternatively the reagents can be accommodated in porous materials such as for example fleeces, papers, membranes and such like which can for example be impregnated with them in a detachable manner. In this case the sample must flow through these materials during which the reagents can be released into the sample before contact with the electrodes. It is also possible to apply individual components of the reagents onto different compartments of the test element, for example the detection reagent on or directly next to the electrode, but a factor X reagent and an activator reagent spatially separated therefrom (e.g. further removed from the electrode) or to impregnate them in different layers (e.g. membranes or fleeces).

According to the invention the test element contains factor X reagent and an activator reagent which converts factor X into factor Xa where the activator reagent is present on the test element at least partially spatially separated from the factor X reagent and in particular is arranged at least partially in front of the factor X reagent in the flow direction of the sample.

In a preferred embodiment this is for example achieved in that the factor X reagent and activator reagent are arranged on the test element in the form of separate reagent lines. These can be present separated from one another or be in contact with one another. An arrangement is particularly preferred in which the reagent line of the activator reagent is arranged at least partially in front of the reagent line of the factor X reagent in the flow direction of the sample and is at least partially in contact with this line and in particular at least partially overlaps this line. In this embodiment the detection reagent is present in a further compartment and in particular in a further reagent line which can, however, at least partially be in contact with the reagent lines of the activator reagent and of the factor X reagent.

In a particularly preferred embodiment the detection reagent is present on the test element together with the activator reagent or the factor X reagent. Since neither the activator reagent nor factor X reagent have activated factor Xa or can alone form factor Xa, the detection reagent can be admixed with one of these reagents without a premature factor Xa-induced degradation of the detection reagent occurring and thus without an undesired interference of the factor Xa inhibitor determination. The addition of the detection reagent to one of the two other reagents allows one reagent compartment to be dispensed with, which enables simpler test element constructions that can be manufactured more cost-effectively. In a particularly preferred embodiment this can for example be achieved by an arrangement in which the reagent line of the activator reagent is arranged at least partially in front of the reagent line of the factor X reagent in the flow direction of the sample and is at least partially in contact with this line and in particular at least partially overlaps this line and the detection reagent is present in a reagent line together with the factor X reagent.

In a further embodiment the test element contains the factor X reagent and activator reagent in a dry chemistry form which causes the conversion of factor X into factor Xa where the activator reagent is present on the test element together with the factor X reagent and optionally also together with the detection reagent and where the conversion of factor X into factor Xa does not take place until contact with the sample. Since the factor X reagent and activator reagent are present on the test element in a dry chemistry form, they are present in a form in which they cannot react with one another. Thus the factor X reagent and activator reagent can be stored together in one compartment without formation of factor Xa. The two reagents cannot react with one another until liquid is added and in particular until contact with the sample liquid and factor X can then be converted into factor Xa.

In a preferred embodiment this is for example achieved by arranging the factor X reagent and activator reagent together on the test element in the form of a common reagent line. In this embodiment the detection reagent can be present in an additional compartment, in particular an additional reagent line which, however, can be at least partially in contact with the reagent line of the combined activator/factor X reagent.

In a particularly preferred embodiment the detection reagent can also be added to the factor X reagent and activator reagent so that all reagents required to determine factor Xa inhibitors can be present in a single compartment, in particular in a single reagent line on the test element. As already stated the use of dry chemistry reagents enables the factor X reagent and activator reagent to be jointly brought together in one compartment without formation of factor Xa. This now also allows the detection reagent to be added to this reagent combination because without activated factor Xa also no premature factor Xa-induced degradation of the detection reagent can take place. In particular the inventive solution enables all reagents required to determine factor Xa inhibitors to be applied in a single compartment which enables simpler test element constructions that can be produced more cost-effectively.

Another aspect of the present invention concerns electrochemical test element analytical systems which contain at least one test element according to the patent claims and an instrument for measuring current or voltage. The use of such instruments enables the detection of the electrogenic thrombin substrate cleavage products that are formed during the course of the factor Xa inhibitor determination and in particular phenylenediamine by means of the current flow occurring at the electrodes. In particularly preferred embodiments the time course of the current flow is measured. The electrochemical determination is preferably carried out quasi-potentiostatically preferably using a two electrode system in which one electrode is connected simultaneously as a reference and counter electrode and the other electrode is connected as a working electrode. A constant voltage is applied to this two-electrode system and the current is measured over time. This method is also referred to as an amperometric measurement procedure. In this procedure the time course of the current is measured and one determines after which period of time from the start of the determination reaction the measured current exceeds a predetermined threshold value. This time period is a measure for the factor Xa-induced thrombin substrate conversion during the course of the coagulation reaction which in turn depends on the amount of factor Xa-inhibitor present in the sample.

In addition to the described amperometric measurement procedure it is also possible to use voltametric measurement procedures. In this case there is not a controlled constant voltage between the electrodes but rather the voltage is changed linearly from an initial value to an end value and subsequently again returned to the initial value. This process can be repeated several times over the entire period of measurement. In the case of voltametric procedures, the current is plotted against the voltage and one obtains nested current-voltage curves (cyclovoltamograms) corresponding to the number of repetitions. With a suitable voltage range oxidation peaks and reduction peaks of the electron carrier are displayed in these curves. The height of these peaks is directly proportional to the concentration of the electron carrier provided no other redox-active substances are co-oxidized or co-reduced in the covered potential range and thus do not additionally contribute to the current. When measuring a change in concentration it may be possible to disregard such an interference. If one now plots the current values of the peak maxima or the areas enclosed by the curves (corresponding to the charge turnover) of the individual current-voltage loops over time one also obtains a picture of the concentration change of the electron carrier over the measurement period in a time frame given by the duration of the cycle. This information can then be used like the amperometric methods to determine the factor Xa inhibitor. Such methods are described for example in WO 01/63271 (US2003/0164113).

The methods and devices according to the invention can be used in particular to determine factor Xa inhibitors in blood samples. In the sense of the present invention the term blood sample includes not only untreated blood (whole blood) but also blood derivatives or blood products which can be obtained from native blood samples by subsequent physical and/or chemical and/or biochemical treatment. Serum or plasma in particular can be regarded as blood derivatives in the sense of the present application. The determination of factor Xa inhibitors can in the sense of the present application be any qualitative, quantitative or semi-quantitative determination of factor Xa inhibitors.

The following are provided for exemplification purposes only and are not intended to limit the scope of the invention described in broad terms above. All references cited in this disclosure are incorporated herein by reference.

EXAMPLES

Example 1

Exemplary Configuration of a Test Element According to the Invention

A possible configuration of a test element according to the invention and its manufacture are described in the following as an example.

The inert carrier material can for example consist of a polyester foil for example a Melinex foil. Electrode structures can be applied to this foil using various methods for example by vapour coating the carrier foil with gold and subsequent laser ablation of the desired electrode structures where other methods for producing these electrode structures are also familiar to a person skilled in the art such as etching methods or printing methods. Optionally certain parts of the electrode structures can subsequently be provided with insulating layers.

The reagents required for the determination are now applied to the carrier material with its electrode structures. Different methods known to a person skilled in the art can be used for this and in particular printing or knife coating methods in which the reagents are applied to the test element in a dissolved form in the form of reagent lines and subsequently the solvent is at least partially removed so that the reagents are present on the test element in a dry chemistry from i.e. inactivated form. Such methods are described for example in WO 01/63271 (US2003/0164113).

In such coating methods the reagents are usually dissolved in a base formulation which contains substances that enable an optimal processing of the reagent solution.

An exemplary composition of such a base formulation is for example (dissolved in redistilled water):

| Concentration * | Substance | Function of the substance | Supplier |
|---|---|---|---|
| 3.5 g/l (0-50 g/l) | Keltrol F | film former | Roche Diagnostics GmbH |
| 5 g/l (0-75 g/l) | hydroxypropyl cellulose | thickener | Hercules |
| 1 g/l (0-10 g/l) | Mega 8 | detergent | Roche Diagnostics GmbH |
| 20 g/l (0-200 g/l) | Mowiol | film former | Kuraray |
| 120 mM (10-500 mM) | base buffer HEPES | pH buffer | Sigma |
| 10 g/l (0.1-100 g/l) | RPLA 4 (serum albumin) | protective protein | Roche Diagnostics GmbH |
| 30 g/l (0-200 g/l) | glycine | stabilizer, solubilizer | Roche Diagnostics GmbH |
| 75 g/l (0-300 g/l) | sucrose | stabilizer, solubilizer | Roche Diagnostics GmbH |

* Number in paranthesis show the range possible according to the invention

Each of the specific reagent components (e.g. thrombin substrate, factor X, activator reagent; individually or also in combination) are now added to this base formulation and applied to the test element in a spatially defined manner for example as reagent lines or reagent spots. After the solvent has been removed, defined and stable reagent lines or reagent spots are now present on the test element in which the reagents can be stored in a stable form over a long period without loss of activity. In preferred embodiments, lateral spacers and a cover foil are also applied which define a capillary channel through which a substantially defined volume of sample can be taken up and transported to the reagent compartments and electrodes.

Example 2

Exemplary Procedure for an Electrochemical Factor Xa Inhibitor Determination Corresponding to the Methods and Devices According to the Invention In order to carry out a factor Xa inhibitor determination, an adequate amount, for example 1-1000 µl and preferably about 10 µl, of the blood to be analyzed is applied to a test element according to the invention that can for example be manufactured according to example 1, in such a manner that it comes into contact with the reagent compartments and electrodes located on the test element. This can preferably be achieved by the presence of a capillary channel on the test element and suitable positioning of the reagent compartments and electrodes on the test element within this capillary channel. In preferred embodiments the sample liquid, test element and/or other devices necessary for the factor Xa inhibitor determination can be maintained at a certain temperature, in particular a temperature of about 37° C. The test element is connected to a suitable measurement device in order to detect the electrochemical detection reactions, for example to a current measurement system which can in particular measure and store the time course of the current flow.

FIG. 1 shows an example of the time course of an electrochemical factor Xa inhibitor determination corresponding to the methods according to the invention. In this case a test element according to Example 1 was used.

The curve shows the time course of the measured current intensity caused by the oxidation of phenylenediamine after its thrombin-induced cleavage from the thrombin substrate. 20 The time t in seconds after applying the blood sample is plotted on the x axis and the current intensity I in nanoamperes determined at the respective time point is plotted on the y axis. The curve firstly passes through a minimum then increases with increasing oxidation of the phenylenediamine, finally reaches a maximum and then decreases continuously due to substrate depletion. The evaluation of such current time courses to determine time parameters which reflect the course of the detection reaction, is for example carried out using a threshold algorithm. This algorithm adds a threshold value to the calculated minimum, for example 60 nA, which is retained for all measurements. The time after reaching the minimum up to which this maximum threshold value is reached, can be determined as the time parameter for thrombin conversion. Since the time parameters for thrombin conversion determined in this manner depend on the activity/concentration of activated factor Xa and this in turn depends on the amount or concentration factor Xa inhibitors that may be present, the time values determined in this manner can thus be used to deduce the presence of a factor Xa inhibitor, whether it exceeds or falls below a certain concentration or the amount or concentration of a factor Xa inhibitor. For this purpose it is for example possible to generate curves using samples of known factor Xa inhibitor concentrations which correlate these concentrations with their time parameters determined according to the invention.

Furthermore, these time parameters that have been determined can be used to determine further parameters that correlate therewith and with the amount of factor Xa inhibitor that may be present, in particular clotting times by using suitable algorithms.

Example 3

Effect of the Arrangement of Reagent Lines on the Test Element Which Contains the Factor X Reagent and an Activator Reagent FIG. 2 shows the results of electrochemical thrombin determinations with different arrangements of reagent lines of an activator reagent and of a detection reagent/factor X reagent combination on a test element. In each case the time course of the measured current intensity is shown where the time t in seconds after applying the blood sample is plotted on the x axis and the current intensity I in nanoamperes determined at the respective time point is plotted on the y axis. In the present example the reagent line of the detection reagent/factor X reagent combination contains 0.8 ml reduced Chromozym TH and 38.1 µl factor X (factor X from American Diagnostics; corresponding to 2 U/ml factor Xa), the reagent line of the activator reagent contains 80 µl Russels viper venom (Russels Viper Venom (RVV-X) from Pentapharm Ltd.) and 0.04% phospholipids (PHL).

The reagent lines were applied in the following variants:

Curve A: Firstly the reagent line of the detection reagent/factor X reagent combination was applied and then the reagent line of the activator reagent was applied over this line.

Curve B: Firstly the reagent line of the detection reagent/factor X reagent combination was applied and then the reagent line of the activator reagent was applied over this line, where the application of the reagent line of the activator reagent was staggered so that at least part of it was in front of the reagent line of the detection reagent/factor X reagent combination in the flow direction of the sample and at least partially overlapped this line.

Both curves in FIG. 2 show no displacement of the minimum towards higher current values and a low initial current. This indicates that premature substrate degradation can be largely suppressed with these preferred methods and devices according to the invention by the at least partial spatial separation of the reagents into two compartments in particular reagent lines.

A displaced application of the reagent line of the activator reagent in front of the reagent line of the detection reagent/factor X reagent combination in the flow direction of the sample (curve B) exhibits lower current maxima and retarded reaction kinetics compared to the application of the reagent line of the activator reagent directly over the reagent line of the detection reagent/factor X reagent combination (curve A). An application of the reagent line of the activator reagent directly over the reagent line of the detection reagent/factor X reagent combination is particularly advantageous for the inventive determination of factor Xa inhibitors and in particular for diagnostic applications primarily due to the more rapid reaction kinetics.

Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for determining the amount an amount of a factor Xa inhibitor in a blood sample comprising:
   (a) contacting a blood sample with a dried reagent comprising a known amount of factor X, an activator reagent that induces the conversion of factor X into factor Xa, and a detection reagent comprising a peptidic thrombin substrate that can be cleaved by thrombin and comprising a carboxyl end that is amidically bound to an electrogenic substance, wherein the reagent comprising factor X is added to the sample in a common step with the addition of the activator reagent to the sample;
   (b) measuring the amount or activity of the electrogenic substance that is cleaved from the thrombin substrate by measuring an electrochemical signal associated with the amount or activity of the electrogenic substance;
   (c) relating the amount or activity of the electrogenic substance to the amount of Xa inhibitor in the sample, thereby determining the amount of the factor Xa inhibitor in the sample.

2. The method of claim 1, wherein the reagent comprising factor X and the activator reagent are present on the element as dry chemistry reagents in spatially separated compartments.

3. The method of claim 1, wherein the activator reagent is arranged at least partially in front of the reagent comprising factor X in a flow direction of the sample.

4. The method of claim 1, wherein the reagent comprising factor X and the activator reagent are present on the element as at least partially separated dry chemistry reagents.

5. The method of claim 1, wherein the reagent comprising factor X and the activator reagent are present on the element as dry chemistry reagents in a common compartment.

6. The method of claim 5, wherein the reagent comprising factor X and the activator reagent are in a single dry chemistry reagent line or spot.

7. The method of claim 1, wherein the detection reagent is added to the sample spatially separated from or at a separate time from the addition of the activator reagent to the sample.

8. The method according to claim 1, wherein the detection reagent is added to the sample after the activator reagent has been added to the sample.

9. The method according to claim 1, wherein the factor Xa inhibitor is selected from the group consisting of unfractionated heparin, fractionated heparin, low-molecular-weight heparin, an indirect selective factor Xa inhibitor, and a direct factor Xa inhibitor.

10. A test element for determining an amount of a factor Xa inhibitor, the element comprising an inert carrier comprising at least two electrodes, a reagent comprising a known amount of factor X, an activator reagent for converting factor X into factor Xa, and a detection reagent that contains at least one peptidic thrombin substrate that can be cleaved by thrombin and comprising a carboxyl end that is amidically bound to an electrogenic substance, wherein the reagent comprising factor X and the activator reagent are present on the element as dry chemistry reagents in a common compartment.

11. The test element of claim 10, wherein the reagent comprising factor X and the activator reagent are in a single dry chemistry reagent line or spot.

12. The test element of claim 10, wherein the Xa inhibitor is selected from the group consisting of unfractionated heparin, fractionated heparin, low-molecular-weight heparin, indirect selective factor Xa inhibitors, and direct factor Xa inhibitors.

13. An analytical system comprising at least one device for measuring current or voltage, and a test element according to claim 10.

14. A test element for determining an amount of a factor Xa inhibitor, the element comprising an inert carrier comprising at least two electrodes and a dried reagent line comprising a reagent comprising a known amount of factor X and an activator reagent for converting factor X into factor Xa, the element further comprising a detection reagent that contains at least one peptidic thrombin substrate that can be cleaved by thrombin and comprising a carboxyl end that is amidically bound to an electrogenic substance.

15. The test element of claim 14, wherein the Xa inhibitor is selected from the group consisting of unfractionated heparin, fractionated heparin, low-molecular-weight heparin, indirect selective factor Xa inhibitors, and direct factor Xa inhibitors.

16. An electrochemical test element analytical system comprising at least one device for measuring current or voltage, and a test element according to claim 14.

* * * * *

UNITED STATES PATENT AND TRADEMARK OFFICE
CERTIFICATE OF CORRECTION

PATENT NO. : 9,594,042 B2
APPLICATION NO. : 14/136769
DATED : March 14, 2017
INVENTOR(S) : Liesel Doerge et al.

It is certified that error appears in the above-identified patent and that said Letters Patent is hereby corrected as shown below:

In the Claims

Claim 1, Column 17, Line 52, please delete "the amount".

Signed and Sealed this
Sixteenth Day of May, 2017

Michelle K. Lee
*Director of the United States Patent and Trademark Office*